United States Patent
Miller

(10) Patent No.: US 10,391,260 B2
(45) Date of Patent: Aug. 27, 2019

(54) HYPODERMIC NEEDLE ASSEMBLY IDENTIFICATION AND RELATED METHODS

(71) Applicant: MEDTECH SYSTEMS INC., Mayer, MN (US)

(72) Inventor: Gary E. Miller, Mayer, MN (US)

(*) Notice: Subject to any disclaimer, the term of this patent is extended or adjusted under 35 U.S.C. 154(b) by 75 days.

(21) Appl. No.: 15/244,227

(22) Filed: Aug. 23, 2016

(65) Prior Publication Data
US 2016/0375198 A1 Dec. 29, 2016

Related U.S. Application Data

(63) Continuation of application No. 13/791,885, filed on Mar. 8, 2013, now Pat. No. 9,446,190.

(60) Provisional application No. 61/608,815, filed on Mar. 9, 2012.

(51) Int. Cl.
| | |
|---|---|
| A61M 5/00 | (2006.01) |
| A61M 5/32 | (2006.01) |
| A61M 5/162 | (2006.01) |
| A61M 5/34 | (2006.01) |
| G06F 19/00 | (2018.01) |

(52) U.S. Cl.
CPC .............. *A61M 5/32* (2013.01); *A61M 5/162* (2013.01); *A61M 5/3205* (2013.01); *A61M 5/3278* (2013.01); *A61M 5/3293* (2013.01); *A61M 5/343* (2013.01); *A61M 5/349* (2013.01); *G06F 19/00* (2013.01); *A61M 2005/3208* (2013.01); *A61M 2205/6009* (2013.01); *A61M 2205/6054* (2013.01); *A61M 2205/6072* (2013.01)

(58) Field of Classification Search
CPC ........ A61M 2005/5073; A61M 5/3205; A61M 2005/3206; A61M 5/349; A61M 2205/6054; A61M 2205/6072; A61M 5/32
See application file for complete search history.

(56) References Cited

U.S. PATENT DOCUMENTS

| | | | | |
|---|---|---|---|---|
| 2007/0073235 A1* | 3/2007 | Estes | ................. | A61M 5/14244 604/151 |
| 2008/0243088 A1* | 10/2008 | Evans | ............... | A61M 5/31525 604/246 |
| 2009/0043253 A1* | 2/2009 | Podaima | ................ | G06Q 10/10 604/67 |
| 2012/0091196 A1* | 4/2012 | Notter | .................. | A61B 5/1405 235/375 |

* cited by examiner

*Primary Examiner* — Rebecca E Eisenberg
(74) *Attorney, Agent, or Firm* — Cardle Patent Law Chtd

(57) ABSTRACT

A needle assembly for a hypodermic syringe is disclosed herein. In various aspects, the needle assembly includes a hub and a needle. A bond secures the needle to the hub, and the bond is configured to break allowing the needle to be withdrawn entirely from the hub upon application of a selected axial force to the needle, in various aspects. The axial force may be less than the tensile strength of the needle. Related methods of use of the needle assembly apparatus are disclosed herein. This Abstract is presented to meet requirements of 37 C.F.R. § 1.72(b) only. This Abstract is not intended to identify key elements of the apparatus and the related methods disclosed herein or to delineate the scope thereof.

20 Claims, 7 Drawing Sheets

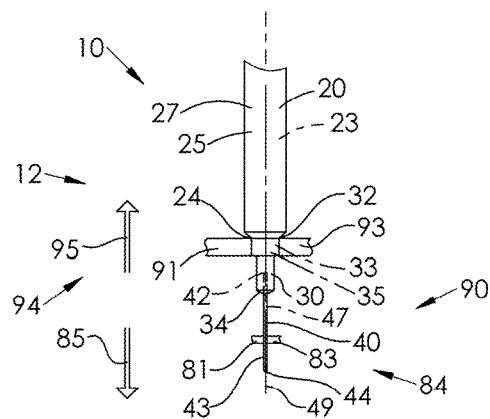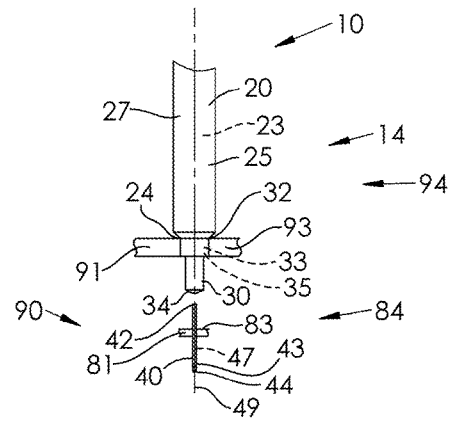
FIG. 1A  FIG. 1B
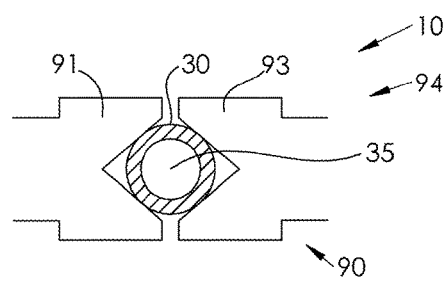
FIG. 1E
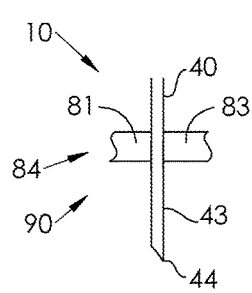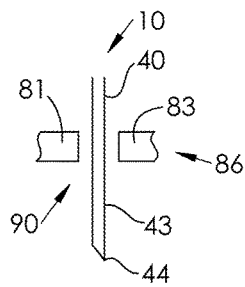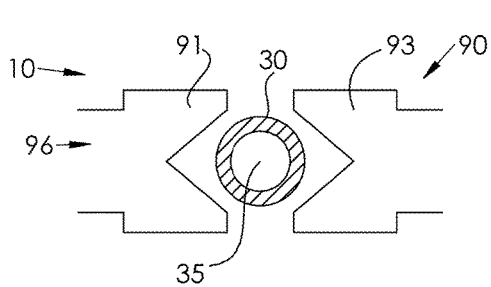
FIG. 1C  FIG. 1D  FIG. 1F

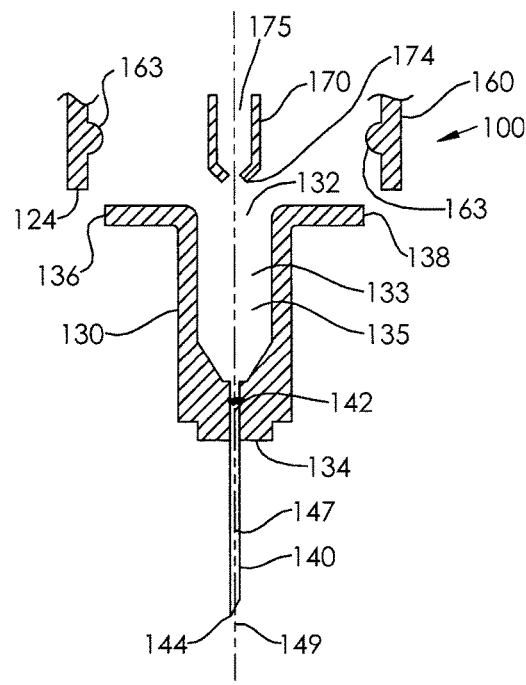
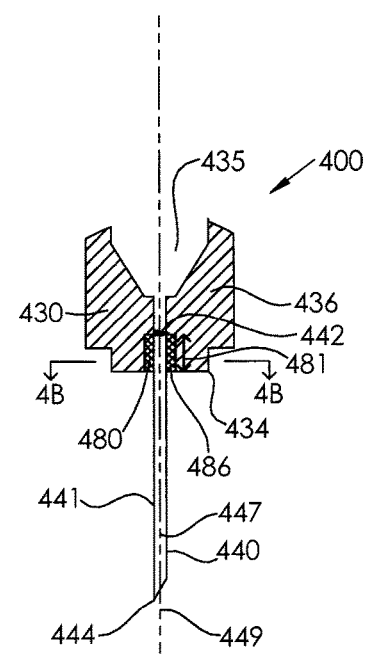
FIG. 3
FIG. 4A
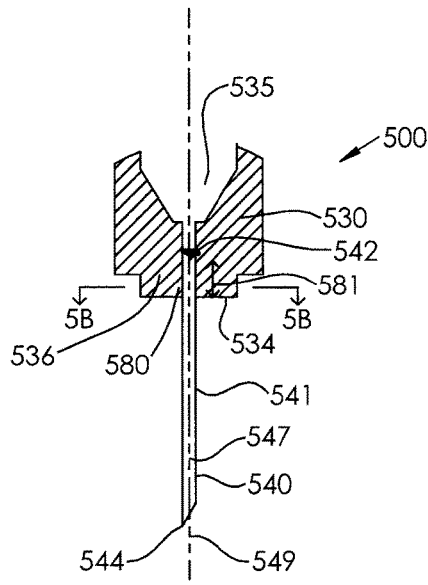
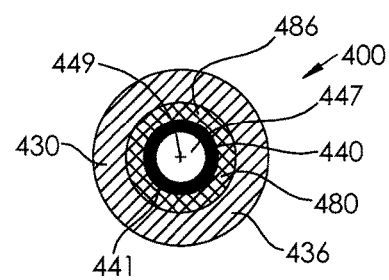
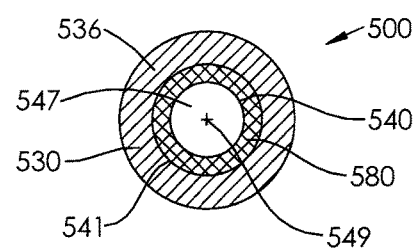
FIG. 5A
FIG. 5B

HYPODERMIC NEEDLE ASSEMBLY IDENTIFICATION AND RELATED METHODS

CROSS-REFERENCE TO RELATED APPLICATIONS

This application is a continuation of U.S. patent application Ser. No. 13/791,885 filed 8 Mar. 2013, which, in turn, claims the priority and benefit of U.S. Provisional Patent Application 61/608,815 filed 9 Mar. 2012, which is hereby incorporated by reference in its entirety herein.

BACKGROUND OF THE INVENTION

Field

The present disclosure relates to medical devices, and, more particularly, needle assemblies as generally used in conjunction with syringes, various holders, and other such devices.

Background

The use and disposal of needle cannula either separate from syringes and various holders or in conjunction with syringes and holders may present a hazard to both the user of the needle cannula as well as to the public at large. For example, needle sticks including various other injuries that may occur during the use or disposal of the needle cannula may transmit various infectious diseases. Personnel involved in collection and disposal of the needle cannula may sustain a needle stick, for example, as a result of handling the needle cannula prior to placement of the needle cannula into a container, failure of the container, or inadvertent exposure to other needle cannulae within the container during deposit of the needle cannula into the container. After disposal, the needle cannula may still present a hazard either in a landfill should portions of the landfill become exposed. In the case of needle cannula disposed of at sea, the needle cannula may, for example, wash up on beaches or pose a hazard to fishermen.

The breaking of the needle cannula from a hub to which the needle cannula is secured leaves a portion of the needle cannula embedded within the hub. The hub with this portion of needle cannula embedded therein may be considered a bio-hazardous material that needs special handling and disposal. Furthermore, the hub with this portion of the needle cannula embedded therein as well as any syringe or holder to which the hub may be attached may not be recycled. As a result, plastic that may form the hub and associated devices may not be recovered for further use, but, rather, must be permanently disposed of.

Various manufacturers have developed safety devices for use in conjunction with needle cannula that may prevent needle sticks. However, these safety devices may require specialized training, may be clumsy to use, and may add cost to the needle cannula and associated syringe or holder. The variety of such safety devices may cause the user to become confused, which may result in a needle stick. Furthermore, when such safety devices are employed, the needle cannula remains secured to the hub so that the needle cannula—hub combination must be disposed of as bio-hazardous waste.

Accordingly, there is a need for improved apparatus as well as related methods that assist the user thereof in the management of needle cannula including other sharps.

SUMMARY OF THE INVENTION

These and other needs and disadvantages cited above are overcome by the apparatus and methods disclosed herein.

Additional improvements and advantages may be recognized by those of ordinary skill in the art upon study of the present disclosure.

A needle assembly for a hypodermic syringe is disclosed herein. In various aspects, the needle assembly includes a hub and a needle. A bond secures the needle to the hub, and the bond is configured to break allowing the needle to be withdrawn entirely from the hub upon application of a selected axial force to the needle, in various aspects. The axial force may be less than the tensile strength of the needle. Related methods of use of the needle assembly apparatus are disclosed herein.

This summary is presented to provide a basic understanding of some aspects of the methods disclosed herein as a prelude to the detailed description that follows below. Accordingly, this summary is not intended to identify key elements of the methods, systems, and compositions of matter disclosed herein or to delineate the scope thereof.

BRIEF DESCRIPTION OF THE DRAWINGS

FIG. 1A illustrates by side view an exemplary implementation of a needle assembly in a first stage of operation;

FIG. 1B illustrates by side view the exemplary implementation of the needle assembly of FIG. 1A in a second stage of operation;

FIG. 1C illustrates by side view portions of the exemplary implementation of the needle assembly of FIG. 1A including needle grippers in an engaged position;

FIG. 1D illustrates by side view portions of the exemplary implementation of the needle assembly of FIG. 1A including needle grippers in a disengaged position;

FIG. 1E illustrates by side view portions of the exemplary implementation of the needle assembly of FIG. 1A including grippers in an engaged position;

FIG. 1F illustrates by side view portions of the exemplary implementation of the needle assembly of FIG. 1A including grippers in a disengaged position;

FIG. 3 illustrates by side cut-away view portions of the exemplary implementation of the needle assembly of FIG. 2B;

FIG. 4A illustrates by side cut-away view portions of another exemplary implementation of a needle assembly;

FIG. 4B illustrates by cross-sectional view portions of the exemplary implementation of the needle assembly of FIG. 4A;

FIG. 5A illustrates by side cut-away view portions of another exemplary implementation of a needle assembly;

FIG. 5B illustrates by cross-sectional view portions of the exemplary implementation of the needle assembly of FIG. 5A;

Figure 1G:
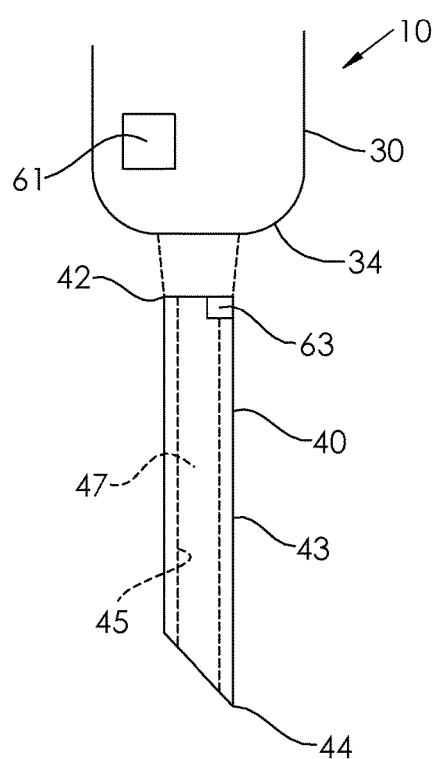
FIG. 1G illustrates by exploded side view portion of the exemplary implementation of the needle assembly of FIG. 1A.

The Figures are exemplary only, and the implementations illustrated therein are selected to facilitate explanation. The number, position, relationship and dimensions of the elements shown in the Figures to form the various implementations described herein, as well as dimensions and dimensional proportions to conform to specific force, weight, strength, flow and similar requirements are explained herein will be understandable to a person of ordinary skill in the art upon study of this disclosure. Where used in the various Figures, the same numerals designate the same or similar elements. Furthermore, when the terms "top," "bottom," "right," "left," "forward," "rear," "first," "second," "inside," "outside," and similar terms are used, the terms should be understood in reference to the orientation of the implementations shown in the drawings and are utilized to facilitate description thereof.

DETAILED DESCRIPTION OF THE INVENTION

A needle assembly is disclosed herein. In various aspects, the needle assembly includes a hub with a needle cannula secured therein. The hub may be attachable to a syringe barrel, or to a holder for the collection of blood or other bodily fluids, or may be formed as a part of such, in various aspects. The needle cannula may be secured within the hub such that the needle cannula may be withdrawn from the hub by an application of an axial force in the direction defined by an axis of a lumen of the needle cannula. The axial force is less than a critical force with the critical force defined as a force that may cause failure of the needle cannula, in various implementations. The needle cannula may be entire withdrawn from the hub so that no portion of the needle cannula remains in the hub, which may allow for recycling or other disposal of the hub that is devoid of the needle cannula.

FIG. 1A illustrates needle assembly 10 in a first stage of operation 12. As illustrated in FIG. 1A, needle assembly 10 includes hub 30 with needle cannula 40 secured therein. Needle cannula 40 has an open proximal end 42 and an open distal end 44 with lumen 47 passing therethrough between the open proximal end 42 and the open distal end 44, in this implementation. Lumen 47 defines axis 49 that passes axially through lumen 47, as illustrated.

Hub 30, as illustrated in FIG. 1A, includes an open proximal end 32 with cavity 33 therein, distal end 34, and passageway 35 passing between proximal end 32 and the proximal end 42 of the needle cannula 40. Cavity 33 forms a portion of passageway 35, in this implementation (see FIG. 3). The proximal end 42 of the needle cannula 40 is joined to the hub 30 such that the needle cannula 40 extends forth from the distal end 34 of the hub 30, and the lumen 47 of the needle cannula 40 is in fluid communication with the passageway 35 of the hub 30.

Needle cannula 40 may be made of metal such as stainless steel. Hub 30 may be made of injection moldable plastic such as polypropylene, polyethylene, polycarbonate, and combinations thereof, in various implementations. Needle cannula 40 may be secured to hub 30 using various manufacturing methods. For example, hub 30 may be made of thermoplastic material integrally formed about the proximal end 42 of needle cannula 40 such that needle cannula 40 is secured to hub 30. As another example, proximal end 42 of needle cannula 40 may be secured within hub 30, at least in part, using epoxy or various other adhesives. In other implementations, needle cannula 40 may be secured within a metal hub by press fit.

Figure 2A:
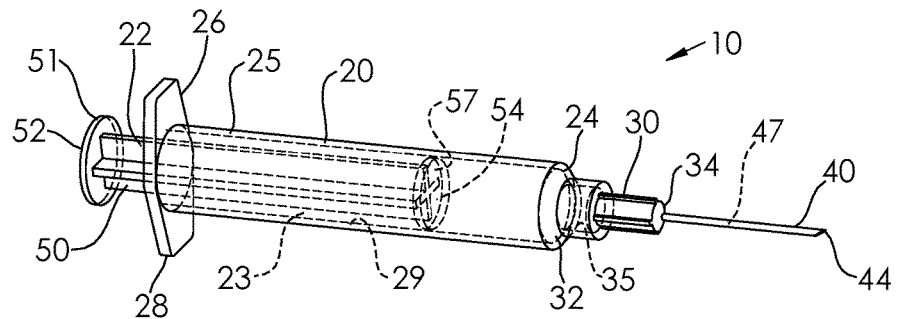
FIG. 2A illustrates by perspective view portions of the exemplary implementation of the needle assembly of FIG. 1A.

As illustrated in FIGS. 1A and 2A, syringe 20 includes syringe barrel 25 having an outside surface 27, an inside surface 29 that defines chamber 23, an open proximal end 22, and a distal end 24. Proximal end 32 of hub 30 is disposed about distal end 24 of syringe barrel 25 such that chamber 23 of syringe barrel 25, passageway 35 including cavity 33 of hub 30, and lumen 47 of needle cannula 40 are in fluid communication with one another. Accordingly, fluid may pass between lumen 47 of needle cannula 40 and chamber 23 of syringe barrel 25 through passageway 35 of hub 30. Hub 30, in this implementation, is formed integrally with syringe barrel 25 so that hub 30 and syringe barrel 25 constitute a unitary structure. In other implementations (see FIGS. 2B, 2C, and 2D), the hub, such as hub 130, 230, 330, may be removably received about the syringe barrel, such as syringe barrels 125, 225. For example, hub 130, 230 may be removably received about the distal ends 124, 224 of the syringe barrels 125, 225, respectively, by threaded engagement or by frictional engagement, respectively.

As illustrated in FIG. 1A, with needle cannula 40 secured within hub 30, syringe 20 is gripped between grippers 91, 93 of needle extractor 90, and needle cannula 40 is gripped between needle grippers 81, 83 of needle extractor 90. Grippers 91, 93 of needle extractor 90 generally engage syringe 20 about hub 30, which is secured to syringe barrel 25 as hub 30 is formed of a piece with syringe barrel 25, in this implementation. With grippers 91, 93 gripping hub 30 and with needle grippers 81, 83 gripping needle cannula 40, grippers 91, 93 may be traversed linearly with respect to axis 49 in the axial direction indicated by arrow 95, needle grippers 81, 83 may be traversed linearly with respect to axis 49 in the axial direction indicated by arrow 85, or both grippers 91, 93 and needle grippers 81, 83 may be traversed linearly with respect to axis 49 in the axial directions indicated by arrows 95, 85, respectively, to withdraw needle cannula 40 entirely from hub 30. Needle extractor 90 may include various mechanisms such as electric motors, guideways, gearing, and so forth, in various implementations, to traverse grippers 91, 93, to traverse needle grippers 81, 83, or to traverse both grippers 91, 93 and needle grippers 81, 83, for example, as generally disclosed in application Ser. No. 12/470,866 (now U.S. Pat. No. 8,201,323) filed on 22 May 2009 by Miller et al. and entitled HYPODERMIC NEEDLE EXTRACTION AND DISPOSAL SYSTEM AND DEVICE, which is hereby incorporated by reference in its entirety herein.

FIG. 1B illustrates needle assembly 10 in a second stage of operation 14 following withdrawal of needle cannula 40 from hub 30 by the traversal of grippers 91, 93, by the traversal of needle grippers 81, 83, or by the traversal of both grippers 91, 93 and needle grippers 81, 83, axially along axis 49. As illustrated in FIG. 1B, proximal end 42 of needle cannula 40 is now exposed, as needle cannula 40 has been extracted from hub 30 leaving substantially no portion of needle cannula 40 remains embedded within hub 30. Needle cannula 40, as illustrated, remains gripped by needle grippers 81, 83, and hub 30 with syringe barrel 25 secured thereto remains gripped by grippers 91, 93

FIG. 1C illustrates needle grippers 81, 83 of needle extractor 90 positioned at position 84 wherein needle grippers 81, 83 are engaged with needle cannula 40 such that needle cannula 40 is held securely between needle grippers 81, 83. FIG. 1D illustrates needle grippers 81, 83 positioned at position 86 wherein needle grippers 81, 83 are set apart from needle cannula 40 such that needle cannula 40 is not engaged with needle grippers 81, 83. Accordingly, needle grippers 81, 83 are positionable between at least position 84 and position 86, in this implementation. Needle grippers 81, 83 may be placed in position 86 as the needle cannula 40 is positioned to be grasped by needle grippers 81, 83. With needle cannula 40 so positioned, needle grippers 81, 83 may be positioned from position 86 into position 84 to secure needle cannula 40 between needle grippers 81, 83. Following withdrawal of the needle cannula 40 from hub 30, needle grippers 81, 83 may be positioned from position 84 to position 86 to release the needle cannula 40. Needle grippers 81, 83 and associated mechanisms (not shown) may be configured to deposit needle cannula 40 into a needle container (not shown) when needle grippers 81, 83 are released from engagement with needle cannula 40 by being positioned from position 84 to position 86. The needle container with needle cannula 40 deposited therein may be disposed of in a suitable manner.

As illustrated in FIGS. 1E and 1F, grippers 91, 93 of needle extractor 90 are positionable between at least position 94 in which position grippers 91, 93 are engaged with hub 30 or other portions of syringe 20 such as syringe barrel 25, and position 96, in which position grippers 91, 93 are disengaged from hub 30 or other portions of syringe 20. FIG. 1E illustrates grippers 91, 93 positioned at position 94 wherein grippers 91, 93 are engaged with hub 30 such that hub 30 is held securely between grippers 91, 93. FIG. 1F illustrates grippers positioned at position 96 wherein needle grippers 91, 93 are set apart from hub 30 such that hub 30 is not engaged with grippers 91, 93. Grippers 91, 93 may be placed in position 96 as the hub 30 is positioned for grasping by grippers 91, 93. With hub 30 so positioned, grippers 91, 93 may be positioned from position 96 into position 94 to secure hub 30 within the grasp of grippers 91, 93. Following withdrawal of the needle cannula 40 from hub 30, grippers 91, 93 may be positioned from position 94 to position 96 to release the syringe barrel 25. Grippers 91, 93 may be configured to deposit hub 30 with syringe barrel 25 attached thereto into a container (not shown) upon release from engagement with hub 30. The container with the combination hub 30 and syringe barrel 25 deposited therein may be recycled or otherwise disposed of. The ability to recycle the syringe barrel 25 and hub 30 may be enhanced, as no metal from the needle cannula 40 remains within hub 30 following extraction of needle cannula 40 from hub 30.

FIG. 1G illustrates portions of needle assembly 10 including hub 30 and needle cannula 40. As illustrated, needle cannula 40 includes outer surface 43 and inner surface 45. Inner surface 45 of needle cannula 40 defines lumen 47 in this implementation.

As illustrated in FIG. 1G, identification tags, such as identification tags 61, 63, may be placed about needle assembly 10, in various implementations. Identification tags 61, 63 may be formed as, for example, laser etched tags, barcodes, various identifying marks, radio frequency identification (RFID) chips that include a unique identifier that uniquely identifies at least the portion of needle assembly 10 to which the identification tags 61, 63 are affixed. Identification tags 61, 63 may be read only, in some implementations, or may have a read/write capability, in other implementations. The read/write capability may allow for multiple read/write cycles.

As illustrated in FIG. 1G, identification tag 61 is affixed to hub 30 and identification tag 63 is affixed to outer surface 43 near the proximal end 42 of needle cannula 40. In other implementations, tag 61 may be affixed to syringe body 20 at various locations, and tag 61 may be variously positioned about needle cannula 40. Identification tags, such as identification tags 61, 63, may be employed to track needle assembly 10 or portions thereof such as the syringe body 20, the hub, 30, or the needle cannula 40, in various implementations, and various numbers of identification tags may be placed about the needle assembly 10.

Identification tags, such as identification tags 61, 63, may be used to track a needle assembly, such as needle assembly 10, from the point of manufacture, through distribution to a medical facility, within an inventory of the medical facility, during dispensation within the medical facility, and at disposal. Identification tag(s) may be used to associate a drug delivered using the needle assembly with the needle assembly. Identification tag(s) may be used to associate the needle assembly with patient records. Identification tag(s) may be used for time stamping of the needle withdrawal from the hub during disposal of the needle assembly. Accordingly, the entire lifespan of the needle assembly from manufacture to use to disposal may be tracked using the identification tag(s). All medical personnel, the drug(s) used with the needle assembly, and the patient may be associated with the needle assembly through use of the identification tag(s).

For example, identification tags 61, 63, may be read in conjunction with the extraction of needle cannula 40 from hub 30 to identify the needle assembly 10 being disposed of, the time of disposal (i.e. the time of extraction of needle cannula 40 from hub 30), and the location of disposal. The needle extractor 90 may include mechanisms that read and/or write to the identification tag(s). The needle extractor 90 may include memory for the storage of information associated with the identification tag(s) such as, for example, the identity of medical personnel operating the needle extractor, the identity of the patient, the drug being delivered to the patient, the time of disposal, or the location of disposal. The needle extractor 90 may be networked to communicate information to or from the identification tag(s) or to communicate information associated with the identification tag(s).

Figure 1H:
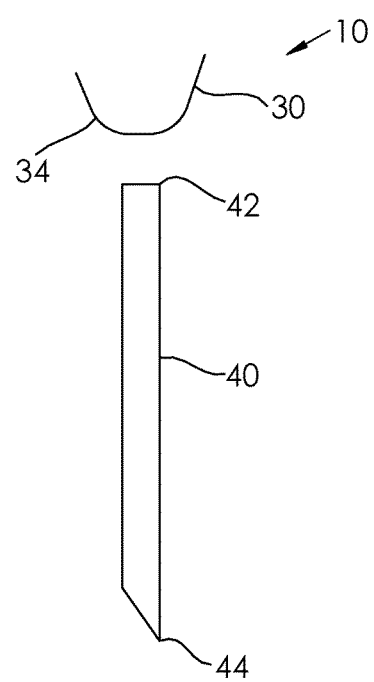
FIG. 1H illustrates by side view portions of the exemplary implementation of the needle assembly of FIG. 1A including the needle cannula following withdrawal of the needle cannula from the hub.

FIG. 1H illustrates needle cannula 40 following extraction of needle cannula 40 from hub 30. As illustrated in FIG. 1H, needle cannula 40 is separated entirely from hub 30 following withdrawal of needle cannula 40 from hub 30, although some debris of hub 30 may cling to needle cannula 40. In implementations that use an adhesive to secure the needle cannula 40 to hub 30 (see, for example, FIGS. 4A & 4B), some adhesive may cling to the needle cannula 40 following extraction of the needle cannula 40 from the hub 30. The needle is separated entirely from the hub 30. Hub 30, as illustrated, may be recycled as hub 30 contains no portion of needle cannula 40 following extraction of needle cannula 40 from hub 30.

FIG. 2A illustrates syringe 20 including chamber 23 of syringe barrel 25. Hub 30, as illustrated, is formed integrally with syringe barrel 25 so that hub 30 and syringe barrel 25 constitute a unitary structure. Chamber 23 of syringe barrel 25, as illustrated, may be accessed through open proximal end 22 of syringe barrel 25. In this implementation, plunger 50 is slidably received within chamber 23 of syringe barrel 25. Proximal end 52 of plunger 50 extends forth from the open proximal end 22 of syringe barrel 25, and proximal end 52 of plunger 50 is formed as circular handle 51 to allow the user to manipulate the position of plunger 50 with respect to syringe barrel 25. Flanges 26, 28 are provided about proximal end 22 of syringe barrel 25 that may enhance the ability of the user to grip the syringe barrel 25 using the fingers.

The distal end 54 of plunger 50 is formed as piston 57. Piston 57 is slidably biased against inside surface 29 of syringe barrel 25 to provide a fluid tight seal between piston 57 and inside surface 29. Accordingly, fluid may be passed between lumen 47 of needle cannula 40 and chamber 23 of syringe barrel 25 through passageway 35 of hub 30 by manipulation of plunger 50, and a user may manipulate plunger 50 generally with handle 51.

Figure 2B:
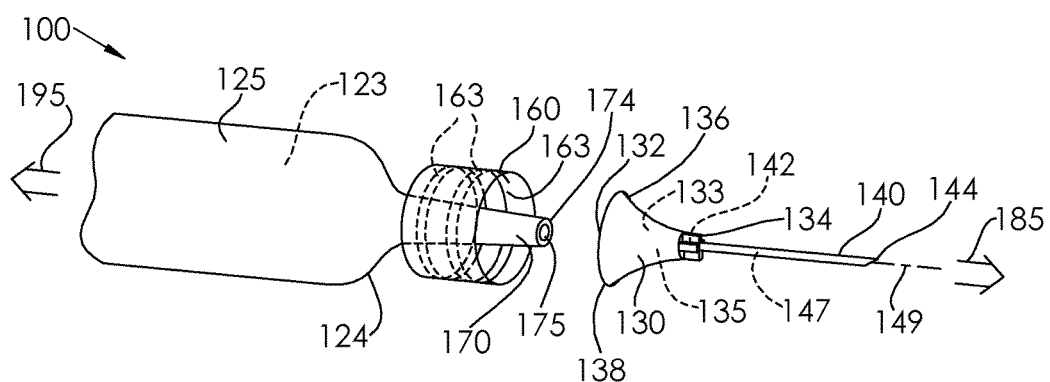
FIG. 2B illustrates by perspective view portions of an exemplary implementation of a needle assembly.

FIG. 2B illustrates needle assembly 100 including hub 130 and needle cannula 140. As illustrated, proximal end 142 of needle cannula 140 is received in hub 130 generally at distal end 134 of hub 130. Hub 130, in this implementation defines internal chamber 133 accessible through open proximal end 132 of hub 130, and passageway 135, which includes chamber 133, communicates fluidly between open proximal end 132 of hub 130 and proximal end 142 of needle cannula 140 into lumen 147. Lumen 147 passes between proximal end 142 and distal end 144, and lumen 147 defines axis 149, as illustrated.

As illustrated in FIG. 2B, syringe body 125 includes collar 160 disposed about distal end 124 with an elongate frusto-conically shaped tip 170 having a conduit 175 therethrough, and tip 170 is centered within collar. Conduit 175 communicates fluidly between distal end 174 of tip 170 and chamber 123 of syringe barrel 125. Threads 163 (threads as used herein includes both helical raised structures and helical grooves configured to receive such helical raised structures) are formed internally about collar 160, and tip 170 protrudes distally, as illustrated. Tip 170 may be received within chamber 133 of hub 130 through the open proximal end 132, and chamber 133 may be shaped to conform to the shape of the frusto-conically shaped tip 170. Hub 130 includes radial projections 136, 138 at proximal end 132 that engage threads 163 to secure hub 130 to tip 170, and, thus, secure hub 130 to syringe barrel 125, in this implementation. In other implementations (not shown), threads may be provided internally within chamber 133 that engage corresponding threads formed on the surface of tip 170. With hub 130 secured to syringe barrel 125 by being received over distal end 174 of tip 170 and having radial projections 136, 138 engaged with threads 163, lumen 147 of needle cannula 140 is in fluid communication with chamber 123 of syringe barrel 125 through passageway 135 of hub 130 and through conduit 175 of tip 170, in this implementation.

In some implementations, with hub 130 of needle assembly 100 secured to syringe body 125, gripers, such as gripers 91, 93, may grip hub 130, various portions of syringe body 125 including collar 160, or combinations thereof such that hub 130 is generally secured by the grippers. Needle grippers, such as needle grippers 81, 83, may grip needle cannula 140 such that needle cannula 140 is secured by the needle grippers. With the hub 130 generally secured to the grippers and the needle grippers gripping needle cannula 140, the grippers may be traversed linearly with respect to axis 149 in the axial direction defined by axis 149 as indicated by arrow 195, the needle grippers may be traversed linearly with respect to axis 149 in the axial direction defined by axis 149 as indicated by arrow 185, or both the grippers and the needle grippers may be traversed linearly with respect to axis 149 in the axial directions indicated by arrows 195, 185, respectively, to withdraw needle cannula 140 entirely from hub 130.

In other implementations, hub 130 of needle assembly 100 may be detached from syringe body 125, and gripers, such as gripers 91, 93, may grip hub 130 such that the grippers secure hub 130. Needle grippers, such as needle grippers 81, 83, may grip needle cannula 140 such that the needle grippers secure needle cannula 140. With the grippers generally gripping hub 130, which is detached from syringe body 125, and the needle grippers gripping needle cannula 140, the grippers may be traversed linearly with respect to axis 149 in the axial direction defined by axis 149 as indicated by arrow 195, the needle grippers may be traversed linearly with respect to axis 149 in the axial direction defined by axis 149 as indicated by arrow 85, or both the grippers and the needle grippers may be traversed linearly with respect to axis 149 in the axial directions indicated by arrows 195, 185, respectively, to withdraw needle cannula 140 entirely from hub 130.

Figure 2C:
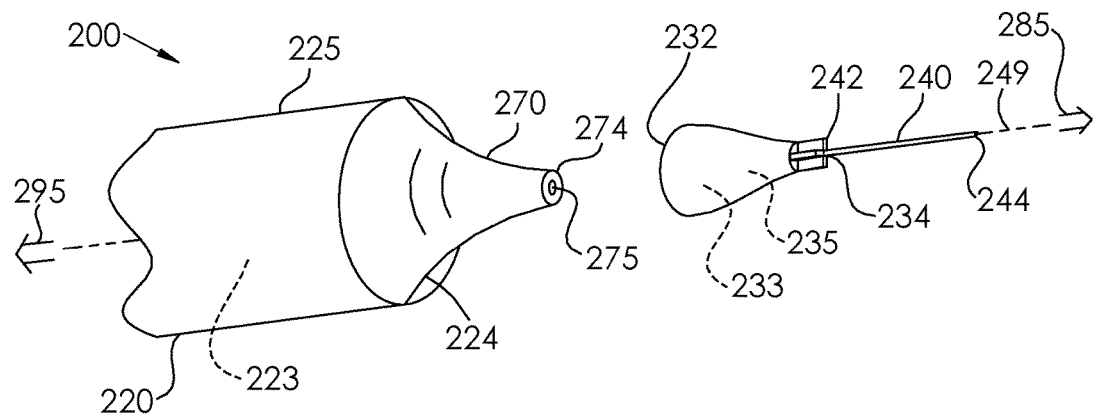
FIG. 2C illustrates by perspective view portions of another exemplary implementation of a needle assembly.

FIG. 2C illustrates needle assembly 200 including hub 230 and needle cannula 240. As illustrated, proximal end 242 of needle cannula 240 is received in hub 230 generally at distal end 234 of hub 230. Hub 230, in this implementation defines internal chamber 233 accessible through open proximal end 232 of hub 230, and passageway 235, which includes chamber 233 communicates fluidly between open proximal end 232 of hub 230 and proximal end 242 of needle cannula 240 into lumen 247. Lumen 247 passes through needle cannula 240 between proximal end 242, and lumen 247 distal end 244, and defines axis 249.

As illustrated in FIG. 2C, an elongate frusto-conically shaped tip 270 having a conduit 275 therethrough forms the distal end 224 of syringe barrel 225. Conduit 275 communicates fluidly between distal end 274 of tip 270 and chamber 223 of syringe barrel 225. Tip 270 may be received within chamber 233 of hub 230 through the open proximal end 232 by insertion of distal end 274 into chamber 233 through the open proximal end 232 of hub 230. In this implementation, chamber 233 of hub 230 is shaped to conform to the shape of the frusto-conically shaped tip 270 to secure the hub 230 to tip 270 by frictional engagement. Accordingly, in this implementation, hub 230 is secured to syringe barrel 225 of syringe 220 by frictional engagement with tip 270. With hub 230 secured to syringe barrel 225 of syringe 220 by being frictionally engaged with tip 270, lumen 247 of needle cannula 240 is in fluid communication with chamber 223 of syringe barrel 225 through passageway 235 of hub 230 and through conduit 275 of tip 270, in this implementation.

In some implementations, with hub 230 secured to syringe body 225 and needle cannula 240 received within hub 230, gripers, such as gripers 91, 93, may grip hub 230, various portions of syringe body 225, or combinations thereof such that hub 230 is generally secured by the grippers. Needle grippers, such as needle grippers 81, 83, may grip needle cannula 240 such that the needle grippers secure needle cannula 240. With hub 230 generally secured to the grippers and the needle grippers gripping needle cannula 240, the grippers may be traversed linearly with respect to axis 249 in the axial direction defined by axis 249 as indicated by arrow 295, the needle grippers may be traversed linearly with respect to axis 149 in the axial direction defined by axis 249 as indicated by arrow 285, or both the grippers and the needle grippers may be traversed linearly with respect to axis 249 in the axial directions indicated by arrows 295, 285, respectively, to withdraw needle cannula 240 entirely from hub 230.

In other implementations, hub 230 of needle assembly 200 with needle cannula 240 received therein may be detached from syringe body 225, and gripers, such as gripers 91, 93, may grip the detached hub 230 such that the grippers secure hub 230. Needle grippers, such as needle grippers 81, 83, may grip needle cannula 240 such that the needle grippers secure needle cannula 240. With the grippers generally gripping hub 230, which is detached from syringe body 225, and the needle grippers gripping needle cannula 240, the grippers may be traversed linearly with respect to axis 249 in the axial direction defined by axis 249 as indicated by arrow 295, the needle grippers may be traversed linearly with respect to axis 249 in the axial direction defined by axis 249 as indicated by arrow 85, or both the grippers and the needle grippers may be traversed linearly with respect to axis 249 in the axial directions indicated by arrows 295, 285, respectively, to withdraw needle cannula 240 entirely from hub 230.

Figure 2D:
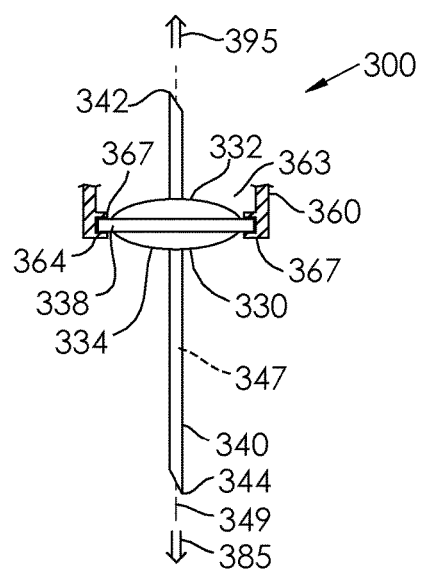
FIG. 2D illustrates by side cut-away view portions of yet another exemplary implementation of a needle assembly.

FIG. 2D illustrates needle assembly 300, which includes needle cannula 340 and hub 330. In this implementation, hub 330 is formed about needle cannula 340 such that needle cannula 340 passes through hub 330. The proximal end 342 of needle cannula 340 extends forth from the proximal end 332 of hub 330 and the distal end 344 of needle cannula 340 extends forth from the distal end 334 of hub 330. Lumen 347 extends the length of needle cannula 340 between proximal end 342 and distal end 344 to communicate fluid between the open proximal end 342 and the open distal end 344. Distal end 344 may be, for example, inserted into the vein or artery of a patient to collect a specimen therefrom. Proximal end 342, for example, may be inserted into various specimen containers (not shown) to allow the collection of the specimen including blood and other fluids and tissues into the specimen container through lumen 347. As a further example, proximal end 342 may be inserted into a container of medicament to deliver the medicament from the container vial lumen 347 to the patient through distal end 344, which is inserted into the patient.

Flange 338 of hub 330 may be engaged with threads 367 of holder 360 to secure hub 330 to the holder 360 generally at the distal end 364 of holder 360 such that the portions of needle cannula 340 that extends forth from proximal end 332 of hub 330 is disposed within chamber 363 of holder 360. Portions of holder 360 proximate distal end 364 in cut-away view are included in this illustration. Holder 360 may be, for example, configured to receive the specimen container within chamber 363 such that the specimen container receives proximal end 342 of needle cannula 340 therein, or holder 360 may be otherwise configured to facilitate the collection of the specimen from the patient, in various implementations.

With needle cannula 340 received within hub 330, gripers, such as gripers 91, 93, may grip hub 230, various portions of holder 360, or combinations thereof such that hub 230 is generally secured by the grippers. Note that the hub 330 may be secured to holder 360, in some implementations, or the hub 330 may be separated from holder 360, in other implementations. Needle grippers, such as needle grippers 81, 83, may grip needle cannula 340 such that the needle grippers secure needle cannula 340. With hub 330 generally secured to the grippers and the needle grippers gripping needle cannula 340, the grippers may be traversed linearly with respect to axis 349 in the axial direction defined by axis 349 as indicated by arrow 395, the needle grippers may be traversed linearly with respect to axis 349 in the axial direction defined by axis 349 as indicated by arrow 385, or both the grippers and the needle grippers may be traversed linearly with respect to axis 349 in the axial directions indicated by arrows 395, 385, respectively, to withdraw needle cannula 340 entirely from hub 330.

FIG. 3 illustrates needle assembly 100 including hub 130 and needle cannula 140. As illustrated in FIG. 3, proximal end 142 of needle cannula 140 is received in hub 130 generally at distal end 134 of hub 130. Hub 130, in this implementation defines internal chamber 133 accessible through open proximal end 132 of hub 130. Passageway 135, which includes chamber 133, communicates fluidly between open proximal end 132 of hub 130 and proximal end 142 of needle cannula 140 into lumen 147, as illustrated.

Tip 170 may be received within chamber 133 of hub 130 through the open proximal end 132, and chamber 133 is shaped to conform to the shape of the frusto-conically shaped tip 170, as illustrated. Radial projections 136, 138 may engage threads 163 to secure hub 130 to tip 170, and, thus, secure hub 130 to syringe barrel 125. With hub 130 secured to syringe barrel 125 by being received over distal end 174 of tip 170 and having radial projections 136, 138 engaged with threads 163, lumen 147 of needle cannula 140 is in fluid communication with chamber 123 of syringe barrel 125 through passageway 135 of hub 130 and through conduit 175 of tip 170, in this implementation.

FIG. 4A illustrates needle assembly 400 including needle cannula 440 and hub 430. Lumen 447 passes between open proximal end 442 and open distal end 444 of needle cannula 440, and lumen 447 defines axis 449. As illustrated in FIG. 4A, proximal end 442 of needle cannula 440 is received within hub 430 generally at the distal end 434 of hub 430 such that lumen 447 may fluidly communicate with passageway 435 of hub 430 through the open proximal end 442 of needle cannula 440. Accordingly, fluid may pass between passageway 435, open proximal end 442 of needle cannula 440, through lumen 447, and through open distal end 444 of needle cannula 440.

As illustrated in FIG. 4A portions of outer surface 441 of needle cannula 440 generally at the proximal end 442 of needle cannula 440 are bonded to hub 430 by bond 480. Bond 480, in this implementation, secures needle cannula 440 to hub 430. As illustrated, bond 480 is interposed between outer surface 441 of needle cannula 440 and hub material 436 of hub 430. The bond material 486 that forms bond 480 may be any of various adhesives including other materials that may differ either mechanically or in composition from the hub material 436 that generally forms hub 430. Bond material 486 may be degraded, for example, by the application of heat, ultraviolet light, ultrasonic vibrations, electrical fields. Accordingly, the application of heat, ultraviolet light, ultrasonic vibrations, electrical fields may be applied to the bond between the hub and the needle cannula to reduce the strength of the bond so the bond fails when selected tension force $F_t$ is applied to needle cannula 440.

The needle cannula 440 is embedded within hub 430 to a length 481, as illustrated, such that bond 480 extends along a portion of needle cannula 440 having length 481. In some implementations, length 481 is chosen so bond 480 fails when tension force $F_t$ is applied to needle cannula 440. Accordingly, needle cannula 440 may be withdrawn from hub 430 upon application of tension force $F_t$ in the axial direction defined by axis 449. Tension force $F_t$ is less than a critical force $F_c$, with critical force $F_c$ being a tensional force that may cause the needle cannula 440 to fail in tension, in various implementations. In some implementations, the bond material 486 that forms bond 480 may be chosen such that bond 480 fails under application of a tension force $F_t$ to needle cannula 440 in the axial direction defined by axis 449 where tension force $F_t$ is less than critical force $F_c$. Bond material 486 may be, for example, heat softenable such that bond 480 looses integrity upon being heated to allow needle cannula 40 to be withdrawn from hub 430 by tension force $F_t$. Bond material 486 may, for example, degrade under application of ultraviolet light, ultrasonic vibrations, electrical fields, and other such stimuli to allow needle cannula 40 to be withdrawn from hub 430 by tension force $F_t$.

Various other combinations of bond material 486 that forms bond 480 and the length 481 to which needle cannula 40 is embedded within hub 430 may be chosen to allow withdrawal of needle cannula 440 from hub 430 when tension force $F_t$ is applied to needle cannula 440 in the axial direction defined by axis 449, where tension force $F_t$ is less than critical force $F_c$, in various implementations.

As illustrated in FIG. 4B, portions of outer surface 441 of needle cannula 440 are bonded to hub 430 by bond 480 to secure needle cannula 440 to hub 430. As illustrated, bond 480 is interposed between outer surface 441 of needle cannula 440 and hub material 436 of hub 430.

FIG. 5A illustrates needle assembly 500 including needle cannula 540 and hub 530. As illustrated in FIG. 5A, proximal end 542 of needle cannula 540 is received within hub 530 generally at the distal end 534 of hub 530 such that lumen 547 may fluidly communicate with passageway 535 of hub 530 through the open proximal end 542 of needle cannula 540. Lumen 547 passes through needle cannula 540 between open proximal end 542 and open distal end 544, and lumen 547 defines axis 549, as illustrated. Accordingly, fluid may pass between passageway 535, open proximal end 542 of needle cannula 540, through lumen 547, and through open distal end 544 of needle cannula 540.

As illustrated in FIG. 5A, portions of outer surface 541 of needle cannula 540 generally at the proximal end 542 of needle cannula 540 are bonded to hub 530 by bond 580. Bond 580 is formed by direct engagement between hub material 536 of hub 530 and outer surface 541 of needle cannula 540, in this implementation. The direct engagement between hub material 536 and outer surface 541 of needle cannula 540, in this implementation, secures needle cannula 540 to hub 530. Hub 530 may be molded or otherwise formed about needle cannula 540 thereby directly engaging the hub material 536 with needle cannula 540 per this implementation.

The needle cannula 540 is embedded within hub 530 to a length 581, as illustrated in FIG. 5A, such that bond 580 extends along a portion of needle cannula 540 having length 581. In some implementations, length 581 is chosen so bond 580 fails when tension force $F_t$ is applied to needle cannula 540 in the axial direction defined by axis 549. In some implementations, the hub material 536 may, for example, be heat softenable, degrade under application of ultraviolet light, ultrasonic vibrations, electrical fields, and other forces or stimuli such that bond 580 looses integrity to allow needle cannula 540 to be withdrawn from hub 530 by selected tension force $F_t$.

Accordingly, needle cannula 540 may be withdrawn from hub 530 upon application of tension force $F_t$ in the axial direction defined by axis 549. Tension force $F_t$ may be less than a critical force $F_c$ with critical force $F_c$ being a tensional force that may cause failure of the needle cannula 440 or otherwise ought not to be exceeded. For example $F_c$ may be selected to be some fraction of the tensile force that might cause failure of the needle cannula 440.

As illustrated in FIG. 5B, portions of outer surface 541 of needle cannula 540 are bonded to hub 530 by bond 580. Bond 580, in this implementation, is formed by direct engagement between hub material 536 of hub 530 and outer surface 541 of needle cannula 540. The direct engagement between hub material 536 and outer surface 541 of bond 580, in this implementation, secures needle cannula 540 to hub 530.

Figure 7:
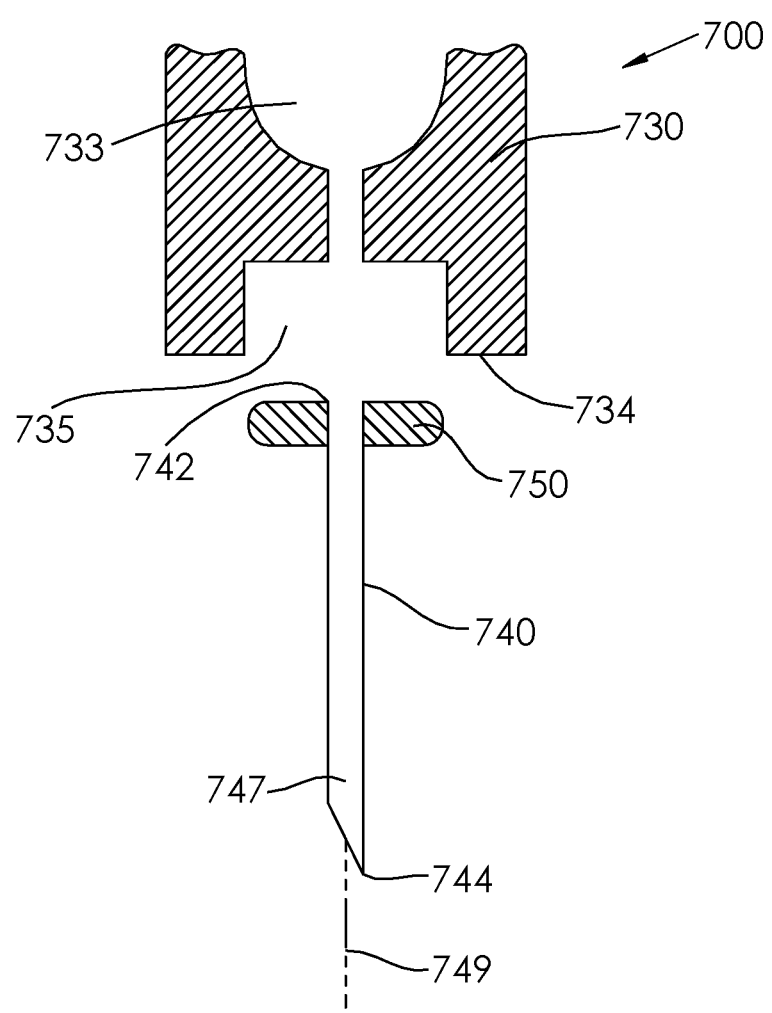

FIG. 7 illustrates needle assembly 700 following withdrawal of needle cannula 740 from hub 730. As illustrated in FIG. 7, slot 735 is formed in distal end 734 of hub 730. Collar 750, which is formed about proximal end 742 of needle cannula 740, is receivable in slot 735 to secure needle cannula 740 to hub 730. Collar 750 may be secured in slot 735, for example, frictionally or by adhesive. Thus, the bond between collar 750 and hub 730 may be, for example, a frictional bond or an adhesive bond. With needle cannula 740 bonded to hub 730 by the securement of collar 750 within slot 735, passageway 733 of hub 730 fluidly communicates with lumen 747 of needle cannula 740 at proximal end 742.

Collar 750 may be pulled out of slot 735 to allow for the withdrawal of needle cannula 740 from hub 730. Upon withdrawal of needle cannula 740 from hub 730, collar 750 may remain attached to the proximal end 742 of needle cannula 740, as illustrated. The needle cannula 740 is entirely removed from hub 730, as illustrated, so that hub 730 is devoid of portions of needle cannula 740 following withdrawal of needle cannula 740 therefrom. An identification tag, such as identification tag 63, may be placed upon collar 750 or upon needle cannula 740 between needle cannula 740 and collar 750, in various implementations.

The bond between collar 750 and hub 730 may be formed such that collar 750 including needle cannula 740 may be withdrawn from hub 730 upon application of tension force $F_t$ in the axial direction defined by axis 749. Tension force $F_t$ is less than a critical force $F_c$, with critical force $F_c$ being a tensional force that may cause the needle cannula 740 to fail in tension. In various implementations, heat, ultraviolet light, ultrasonic vibrations, electrical fields, and suchlike may be applied to hub 730, collar 750, or hub 730 and collar 750 to alter the bond between hub 730 and collar 750 in order to reduce the force $F_t$ required to withdraw the needle cannula 740 from the hub 730 such that $F_t \le F_c$. At least portions of hub 730 or collar 750 may be formed of materials that may be altered by the application of heat, ultraviolet light, ultrasonic vibrations, electrical fields, and suchlike thereto thereby altering the bond between hub 730 and collar 750.

Figure 6A:
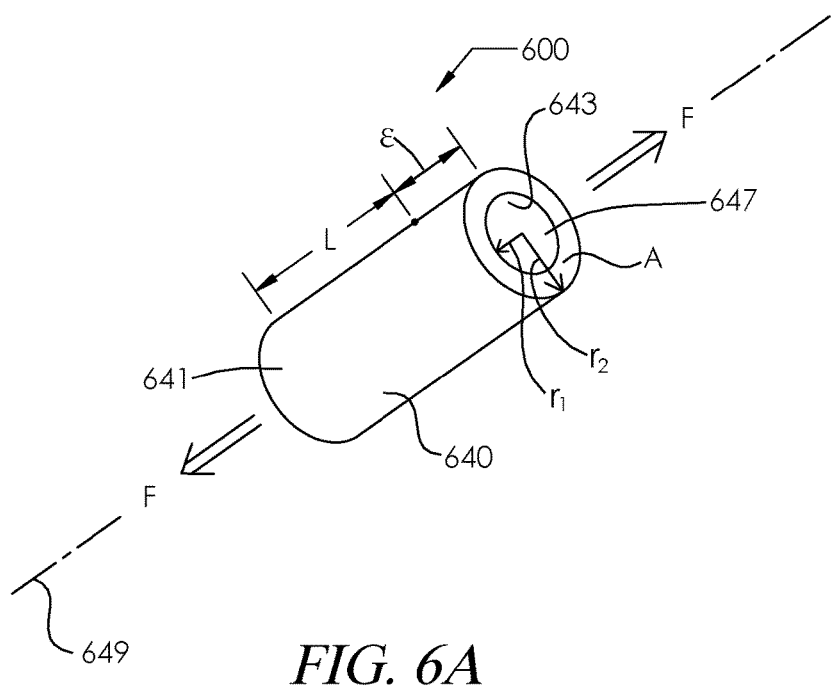
FIG. 6A illustrates by perspective view portions of an exemplary needle cannula of an exemplary needle assembly.
Figure 6B:
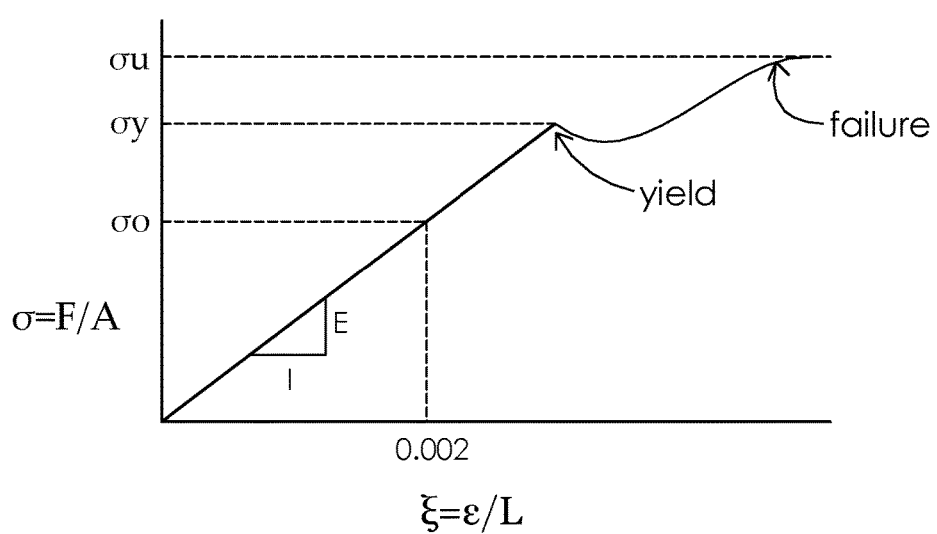
FIG. 6B illustrates by Cartesian plot an exemplary relationship between axial stress and axial strain for the exemplary needle cannula of FIG. 6A; and, FIG. 7 illustrates by side cut-away view portions of another exemplary implementation of a needle assembly.

FIGS. 6A and 6B illustrate an exemplary stress vs. strain curve for needle cannula 640 of needle assembly 600. Needle cannula section 640 of needle assembly 600, as illustrated in FIG. 6A, includes lumen 647 which defines axis 649. Needle cannula section 640 has length L and an annular cross-sectional area $A=\pi(r_2^2-r_1^2)$ where $r_2$ is the radius of the outer surface 641 of needle cannula section 640 and $r_1$ is the radius of wall 643 of lumen 647, respectively, with respect to axis 649. Under axial force F, needle cannula section 640 elongates by amount $\varepsilon$, as illustrated. The axial stress $\sigma$ produced by axial force F may be calculated as $\sigma=F/A$, and the corresponding strain $\xi=\varepsilon/L$. A resulting exemplary relationship between stress $\sigma$ and strain $\xi$ is illustrated in FIG. 6B.

As illustrated in FIG. 6B, the relationship between stress $\sigma$ and strain $\xi$ is linearly elastic with $\xi=\sigma/E$ over the range $0 \le \sigma \le \sigma_y$, where E is Young's modulus of elasticity. At $\sigma \ge \sigma_y$, where $\sigma_y$ is the yield stress, needle cannula section 640 deforms plastically. Needle cannula section 640 fails at $\sigma=\sigma_u$, where $\sigma=\sigma_u$ is the ultimate stress. Accordingly, the critical force $F_c$ may be defined in terms of the ultimate stress $\sigma_u$, the yield stress $\sigma_y$, or an offset stress $\sigma_o$, which is defined in FIG. 6B as the stress that corresponds to strain $\xi=0.002$. Defining the critical force $F_c$ in terms of $\sigma_0$ may be useful for certain stainless steel and other metal alloys that may not exhibit a yield point. The offset stress $\sigma_0$ may be defined in terms of other strain values (e.g. $\xi=0.001$) in various other implementations. Use of an offset stress may be appropriate in materials such as stainless steel of which the needle cannula is likely composed.

Thus, the critical force $F_c$ may be defined variously, for example, as $F_c=\sigma_u$, or $F_c=\sigma_y$ A, or $F_c=\sigma_o$ A. The tension force $F_t$ applied to the needle cannula, such as needle cannula 40, 140, 240, 340, 440, 540, 740 to withdraw the needle cannula from the hub, such as hub 30, 130, 230, 330, 430, 530, 730 is constrained such that $F_t \leq F_c$ in various implementations. The needle cannula is retained in the hub in such a way that application of tension force $F_t$ to the needle cannula will withdraw the needle cannula from the hub when $F_t \leq F_c$ in various implementations.

Table I lists values for needle gauge, outside diameter, inside diameter, cross-sectional area A, the force F corresponding to $\xi=0.002$ (F=$\sigma_o$ A), the force F at yield (F=$\sigma_y$ A), and the force F at ultimate stress (F=$\sigma_u$ A). Values for the outside diameter and the inside diameter were provided by Medical Tube Technology, Inc. of 134 Adams Street, Royersford, Pa. 19468. The material properties used were 0.2% yield stress $\sigma_o$=193 MPa, ultimate tensile strength of $\sigma_u$=517 MPa, which are values for type 304/304L stainless steel as provided by Carpenter Technology Corp. of 2 Meridian Boulevard, Wyomissing, Pa., 19610-1339. A value of $\sigma_y$=290 MPa was used for the yield stress. These material properties, as well as the values in Table I, are exemplary only, as there may be variations in the dimensions and material properties between manufacturers, materials, and so forth. Note that values used herein may be generally taken to engineering accuracy, which may be 3-4 decimal places. Physical values may be accurate to within 5% to 10%. When used herein, words such as "approximate" or "about" may reflect this level of accuracy.

TABLE I

| Needle gauge | O.D. (mm) | I.D. (mm) | x-sect area (mm²) | Force at $\xi$ = 0.002 (N) | Force at Yield Stress $\sigma_y$ (N) | Force at Ultimate Stress $\sigma_u$ (N) |
|---|---|---|---|---|---|---|
| 7 | 4.572 | 3.81 | 5.02E+00 | 9.68E+02 | 1.45E+03 | 2.59E+03 |
| 8 | 4.191 | 3.429 | 4.56E+00 | 8.80E+02 | 1.32E+03 | 2.36E+03 |
| 9 | 3.759 | 2.997 | 4.04E+00 | 7.80E+02 | 1.17E+03 | 2.09E+03 |
| 10 | 3.404 | 2.692 | 3.41E+00 | 6.58E+02 | 9.89E+02 | 1.76E+03 |
| 11 | 3.048 | 2.388 | 2.82E+00 | 5.44E+02 | 8.17E+02 | 1.46E+03 |
| 12 | 2.769 | 2.159 | 2.36E+00 | 4.56E+02 | 2.96E+02 | 1.22E+03 |
| 13 | 2.413 | 1.803 | 2.02E+00 | 3.90E+02 | 2.35E+02 | 1.04E+03 |
| 14 | 2.108 | 1.600 | 1.48E+00 | 2.86E+02 | 2.07E+02 | 7.65E+02 |
| 15 | 1.829 | 1.372 | 1.15E+00 | 2.22E+02 | 1.52E+02 | 5.94E+02 |
| 16 | 1.651 | 1.194 | 1.02E+00 | 1.97E+02 | 1.05E+02 | 5.28E+02 |
| 17 | 1.473 | 1.067 | 8.10E-01 | 1.56E+02 | 9.27E+01 | 4.19E+02 |
| 18 | 1.27 | 0.838 | 7.15E-01 | 1.38E+02 | 7.84E+01 | 3.70E+02 |
| 19 | 1.067 | 0.686 | 5.25E-01 | 1.01E+02 | 1.52E+02 | 2.71E+02 |
| 20 | 0.9081 | 0.603 | 3.62E-01 | 6.99E+01 | 1.05E+02 | 1.87E+02 |
| 21 | 0.8192 | 0.514 | 3.20E-01 | 6.17E+01 | 9.27E+01 | 1.65E+02 |
| 22 | 0.7176 | 0.413 | 2.70E-01 | 5.22E+01 | 7.84E+01 | 1.40E+02 |
| 23 | 0.6414 | 0.337 | 2.34E-01 | 4.51E+01 | 6.78E+01 | 1.21E+02 |
| 24 | 0.5652 | 0.311 | 1.75E-01 | 3.38E+01 | 5.07E+01 | 9.04E+01 |
| 25 | 0.5144 | 0.26 | 1.55E-01 | 2.99E+01 | 4.49E+01 | 8.00E+01 |
| 26 | 0.4636 | 0.26 | 1.16E-01 | 2.23E+01 | 3.36E+01 | 5.98E+01 |
| 27 | 0.4128 | 0.21 | 9.92E-02 | 1.91E+01 | 2.88E+01 | 5.13E+01 |
| 28 | 0.362 | 0.184 | 7.63E-02 | 1.47E+01 | 2.21E+01 | 3.95E+01 |
| 29 | 0.3366 | 0.184 | 6.24E-02 | 1.20E+01 | 1.81E+01 | 3.23E+01 |
| 30 | 0.3112 | 0.159 | 5.62E-02 | 1.08E+01 | 1.63E+01 | 2.91E+01 |
| 31 | 0.2604 | 0.133 | 3.94E-02 | 7.60E+00 | 1.14E+01 | 2.04E+01 |
| 32 | 0.235 | 0.108 | 3.42E-02 | 6.60E+00 | 9.92E+00 | 1.77E+01 |
| 33 | 0.2096 | 0.108 | 2.53E-02 | 4.89E+00 | 7.35E+00 | 1.31E+01 |
| 34 | 0.1842 | 0.0826 | 2.13E-02 | 4.11E+00 | 6.17E+00 | 1.10E+01 |

Sample Calculations For Table I

For the 31 gauge needle, as calculated in Table I, the cross-sectional area:

$$A=\pi((0.2604 \text{ mm})^2-(0.133 \text{ mm})^2)/4=0.0394 \text{ mm}^2=3.94\times10^{-8} \text{ m}^2$$

Then,

At the offset strain $\tau=0.002$, the corresponding force:

$$F=(1.93\times10^8 \text{ N/m}^2)(3.94\times10^{-8} \text{ m}^2)=7.60 \text{ N}$$

At yield $\sigma=\sigma_y$ and the corresponding force:

$$F=(2.90\times10^8 \text{ N/m}^2)(3.94\times10^{-8} \text{ m}^2)=11.4 \text{ N}$$

At ultimate strength $\sigma=\sigma_u$ and the corresponding force:

$$F=(5.17\times10^8 \text{ N/m}^2)(3.94\times10^{-8} \text{ m}^2)=20.4 \text{ N}$$

In operation, the needle assembly, such as needle assembly 10, 100, 200, 300, 400, 500, 600, 700 may be deployed in a first stage of operation, such as first stage of operation 12, in which a needle cannula, such as needle cannula 40, 140, 240, 340, 440, 540, 740 is secured within a hub, such as hub 30, 130, 230, 330, 430, 530, 730. With the needle assembly in the first stage of operation, the hub may be secured by being grasped by grippers, such as grippers 91, 93 including other structures and mechanisms that may secure the hub, of a needle extractor, such as needle extractor 90. The hub may be secured directly by the grippers, in some implementations. In other implementations, the grippers may secure the hub by, for example, securing the syringe barrel, such as syringe barrel 25, 125, 225, or the holder, such as holder 360, to which the hub is attached. In various implementations, the hub may be removed from the syringe barrel or the holder, and the grippers may secure the hub with the syringe barrel or holder removed therefrom. In some implementations, the syringe barrel or holder may be removed from the hub when the hub is secured by the grippers—i.e. the grippers may hold the hub to allow the user to remove the syringe barrel or holder from the hub. With the needle assembly in the first stage of operation, the needle cannula may be secured by being grasped by needle grippers, such as needle grippers 81, 83, including other structures and mechanisms that may secure the needle cannula, of the needle extractor. Various sheaths, covers, and so forth may be placed between the needle cannula and the needle grippers as the needle grippers grasp the needle cannula.

With the hub is secured by the grippers and the needle cannula secured by needle grippers, the needle grippers may be traversed linearly with respect to an axis defined by the needle cannula, such as axis 49, 149, 249, 349, 449, 549, 649, 749, to withdraw the needle cannula from the hub. The needle grippers may be traversed in the axial direction, for example, as indicated by arrows 85, 185, 285, 385. In this exemplary mode of operation, the hub is fixed and the needle grippers are traversed linearly to withdraw the needle cannula from the hub. Thus a linear tensional force is applied along the needle cannula in the axial direction to withdraw the needle cannula from the hub.

Alternatively, with the hub is secured by the grippers and the needle cannula is secured by the needle grippers, the grippers may be traversed linearly with respect to the axis defined by the needle cannula to withdraw the needle cannula from the hub. The grippers may be traversed in the axial direction, as indicated, for example, by arrows 95, 195, 295, 395. The needle grippers are fixed and the grippers are traversed to withdraw the needle cannula from the hub, in this exemplary mode of operation.

In yet another exemplary mode of operation, with the hub is secured by the grippers and the needle cannula is secured by the needle grippers, both the grippers and the needle grippers may be traversed linearly with respect to the axis defined by the needle cannula to withdraw the needle cannula from the hub.

Withdrawal of the needle cannula from the hub positions the needle assembly from the first stage of operation into a second stage of operation such as second stage of operation 14. Accordingly, when the needle cannula has been withdrawn from the hub, the needle assembly is placed in the second stage of operation.

As the needle assembly is positioned from the first stage of operation into the second stage of operation, tension force $F_t$ is applied axially to the needle cannula. The tension force $F_t$ may be selected to be less than critical force $F_c$ with critical force $F_c$ being a tensional force that may cause failure of the needle cannula 440. $F_c$ may be defined in terms of offset stress $F_c = \sigma_o A$, yield stress $F_c = \sigma_y A$, ultimate stress $F_c = \sigma_u A$, or some fraction thereof, such as $F_c = 0.25 \sigma_u A$ (e.g. the critical force $F_c$ is defined as ¼ of the ultimate strength $\sigma_u A$). The critical force $F_c$ may be defined, for example, as a fraction (e.g. ¼, ⅕, . . . ) of yield strength $\sigma_y A$, ultimate strength $\sigma_u A$, offset strength $\sigma_o A$, and so forth, so as to include a suitable margin of safety, in various implementations.

In some implementations, the length of the portion of the needle cannula embedded in the hub, such as length 481, is chosen such that the bond between the needle cannula and the hub, such as bond 480 fails when the selected tension force $F_t$ is applied to needle cannula 440 with $F_t \leq F_c$. In some implementations, the bond material, such as bond material 486, that forms the bond may be chosen such that the bond fails when tension force $F_t$ is applied to the needle cannula in the axial direction. In various implementations, heat, ultraviolet light, ultrasonic vibrations, electrical fields, and suchlike may be applied to the hub including the bond between the hub and the needle cannula prior to or concurrent with the withdrawal of the needle cannula from the hub in order to reduce the force $F_t$ required to withdraw the needle cannula from the hub such that $F_t \leq F_c$.

Following the withdrawal of the needle cannula from the hub, the needle cannula may be placed in various containers and subsequently disposed of. The hub including any syringe, holder, or other such apparatus attached thereto may be collected and recycled or otherwise disposed of following the withdrawal of the needle cannula from the hub.

The foregoing discussion along with the Figures discloses and describes various exemplary implementations. These exemplary implementations are not meant to limit the scope of coverage, but, instead, to assist in understanding the context of the language used in this specification and in the claims. Upon study of this disclosure and the exemplary implementations herein, one of ordinary skill in the art may readily recognize that various changes, modifications and variations can be made thereto without departing from the spirit and scope of the inventions as defined in the following claims.

The invention claimed is:

1. A needle assembly, comprising:
   a needle cannula with a distal end and a proximal end, the needle cannula has an outer surface defining a circumference and the needle cannula defines an axis that is linear between the distal end and the proximal end; and,
   an identification tag comprising machine readable information that uniquely identifies said needle assembly, the identification tag affixed to a portion of the outer surface, an attachment between the identification tag and the outer surface comprising less than the circumference.

2. The apparatus of claim 1, further comprising:
   a syringe barrel engageable with the needle cannula; and
   a second identification tag comprising machine readable information affixed to the syringe barrel.

3. The apparatus of claim 1, the identification tag is affixed at the proximal end of the needle cannula.

4. The apparatus of claim 1, the identification tag comprises a radio frequency identification chip (RFID).

5. The apparatus of claim 4, the RFID has read only capability.

6. The apparatus of claim 4, the RFID has read-write capability.

7. The apparatus of claim 1, wherein the identification tag is formed as an etching upon the outer surface.

8. The apparatus of claim 7, wherein the etching comprises a bar code.

9. The apparatus of claim 1, wherein the identification tag is in operable communication with a digital network.

10. The apparatus of claim 1, wherein the identification tag is utilized to track said needle assembly from a point of manufacture, distribution to a medical facility, within an inventory of the medical facility, during dispensation within the medical facility, and at disposal.

11. The apparatus of claim 1, the machine readable information is used to associate a drug delivered using said needle assembly with said needle assembly.

12. The apparatus of claim 1, the machine readable information is used to associate a patient with said needle assembly.

13. The apparatus of claim 1, the machine readable information is used to associate a user of said needle assembly with said needle assembly.

14. The apparatus of claim 1, further comprising a collar disposed about the proximal end of the needle cannula for securement of the needle cannula to a hub.

15. A needle assembly apparatus, comprising:
   a needle cannula that defines an outer surface, a portion of the outer surface engageable with a hub by embedment of a length of the needle within the hub to form a sole engagement of the needle cannula with the hub, the length selected to allow withdrawal of an entirety of the needle cannula from the hub by disengagement of the portion of the length from the hub upon application of a selected tension force to the needle cannula along the axis by only axial motion between a needle gripper releaseably engaged with the outer surface of the needle cannula and a gripper engaged with the hub, the selected tension force less than a force causing failure of the needle cannula, the needle gripper being positionable between the engaged position in releaseable engagement with the outer surface of the needle cannula and a released position disengaged from the needle cannula; and an identification tag secured to the needle cannula to uniquely identify the needle cannula.

16. The apparatus of claim 15, the identification tag comprises a radio frequency identification chip (RFID).

17. The apparatus of claim 16, the RFID has read only capability.

18. The apparatus of claim 16, the RFID has read-write capability.

19. The apparatus of claim 15, the identification tag is formed as an etching upon the outer surface.

20. The apparatus of claim 15, the identification tag in operable communication with a digital network.

* * * * *